US009138453B2

(12) United States Patent
Zhao-Wilson

(10) Patent No.: US 9,138,453 B2
(45) Date of Patent: Sep. 22, 2015

(54) NUTRIENT COMBINATIONS FOR AFFECTING AN AGING PROCESS

(71) Applicant: BioMarker Pharmaceuticals, Inc., San Jose, CA (US)

(72) Inventor: Xi Zhao-Wilson, Los Gatos, CA (US)

(73) Assignee: BioMarker Pharmaceuticals, Inc., San Jose, CA (US)

(*) Notice: Subject to any disclaimer, the term of this patent is extended or adjusted under 35 U.S.C. 154(b) by 0 days.

(21) Appl. No.: 14/513,136

(22) Filed: Oct. 13, 2014

(65) Prior Publication Data
US 2015/0104393 A1 Apr. 16, 2015

Related U.S. Application Data

(60) Provisional application No. 61/890,839, filed on Oct. 14, 2013.

(51) Int. Cl.
*A61K 36/82* (2006.01)
*A61K 31/05* (2006.01)
*A61K 36/87* (2006.01)
*A61K 31/352* (2006.01)
*A61K 31/09* (2006.01)
*A61K 31/122* (2006.01)
*A61K 31/385* (2006.01)
*A61K 31/225* (2006.01)
*A61K 31/4745* (2006.01)
*A61K 31/355* (2006.01)
*A61K 31/593* (2006.01)
*A61K 31/5685* (2006.01)
*C12Q 1/68* (2006.01)
*A61K 36/00* (2006.01)
*A61K 31/205* (2006.01)

(52) U.S. Cl.
CPC ............. *A61K 36/82* (2013.01); *A61K 31/05* (2013.01); *A61K 31/09* (2013.01); *A61K 31/122* (2013.01); *A61K 31/205* (2013.01); *A61K 31/225* (2013.01); *A61K 31/352* (2013.01); *A61K 31/355* (2013.01); *A61K 31/385* (2013.01); *A61K 31/4745* (2013.01); *A61K 31/5685* (2013.01); *A61K 31/593* (2013.01); *A61K 36/00* (2013.01); *A61K 36/87* (2013.01); *C12Q 1/6876* (2013.01); *C12Q 2600/106* (2013.01); *C12Q 2600/136* (2013.01); *C12Q 2600/158* (2013.01)

(58) Field of Classification Search
CPC ...................................................... A61K 36/00
USPC ........................................................ 424/725
See application file for complete search history.

(56) References Cited

U.S. PATENT DOCUMENTS

| 6,417,233 | B1 | 7/2002 | Sears et al. |
|---|---|---|---|
| 7,678,404 | B2 | 3/2010 | Shiraishi et al. |
| 7,897,169 | B2 | 3/2011 | Ueda et al. |
| 8,343,517 | B1 | 1/2013 | Bezzek |
| 8,658,161 | B2 | 2/2014 | Fantuzzi |
| 8,821,925 | B2 | 9/2014 | Fantuzzi |
| 8,835,396 | B2 | 9/2014 | Verlaan et al. |
| 2002/0198177 | A1 | 12/2002 | Horrobin |
| 2009/0163580 | A1 | 6/2009 | Yatcilla et al. |
| 2010/0021573 | A1 | 1/2010 | Gonzalez et al. |
| 2011/0123651 | A1 | 5/2011 | Mower et al. |
| 2012/0269868 | A1 | 10/2012 | Faerstein |
| 2013/0017283 | A1 | 1/2013 | Zemel et al. |
| 2013/0129821 | A1 | 5/2013 | Fantuzzi |

FOREIGN PATENT DOCUMENTS

| CN | 101015350 | 8/2007 |
|---|---|---|
| JP | 2010126463 | 6/2010 |
| TW | 201004637 | 2/2010 |
| WO | WO-03028714 | 10/2003 |
| WO | WO-2005067972 | 7/2005 |
| WO | WO-2009039195 | 3/2009 |

OTHER PUBLICATIONS

International Search Report and Written Opinion mailed Feb. 20, 2015, PCT Appln. No. PCT/US2014/06510, 34 pages.
Acosta, S., et al., "NT-020, a Natural Therapeutic Approach to Optimize Spatial Memory Performance and Increase Neural Progenitor Cell Proliferation and Decrease Inflammation in the Aged Rat", *Rejuvenation Research*, vol. 13, No. 5, (Oct. 1, 2010), pp. 581-588.
Aksenov, Vadim, et al., "A complex dietary supplement augments spatial learning, brain mass, and mitochondrial electron tansport chain activity in aging mice", *Age: Journal of the American Aging Association*, vol. 35, published online Nov. 27, 2011, (2013), pp. 23-33
Banks, Ruth, et al., "Vitamin E supplementation and mammalian lifespan", *Molecular Nutrition & Food Research*, vol. 54, No. 5, (May 1, 2010), pp. 719-725.
Chen, C. F., "Effects of dehydroepiandrosterone on body mass and memory and learning performances in aging rats", *EMBASE Database*, Database Accession No. EMB-2006191719, abstract, (Mar. 15, 2006).

(Continued)

*Primary Examiner* — Michael Meller
(74) *Attorney, Agent, or Firm* — Blakely Sokoloff Taylor & Zafman LLP

(57) ABSTRACT

A composition comprising an effective amount of a combination of mitochondrial nutrients sufficient to affect mitochondrial function. A method of affecting an aging process in a subject comprising administering to a subject an effective amount of a combination of mitochondrial nutrients sufficient to affect an aging process. A method of identifying a combination of mitochondrial nutrients sufficient to affect an aging process in a subject, the method comprising: administering a combination of mitochondrial nutrients to a subject; and determining whether the mitochondrial nutrients affect an aging process in the subject.

6 Claims, 15 Drawing Sheets

(56) References Cited

OTHER PUBLICATIONS

Li, Qiong, et al., "Chronic green tea catechins administration prevents oxidative stress-related brian aging in C57BL/6J mice", *Brain Research*, vol. 1353, (Sep. 24, 2010), pp. 28-35.

Linnane, Anthony W., et al., "Human Aging and Global Function of Coenzyme Q10", *Ann. N.Y. Acad. Sci.*, vol. 959, (2002), pp. 396-411.

Liu, J., et al., "Reducing mitochondrial decay with mitochondrial nutrients to delay and treat parkinson's disease", *Journal of Neurological Sciences*, vol. 248, No. 1-2, (Oct. 1, 2006), p. 273.

Liu, Jiankang, "The Effects and Mechanisms of Mitochondrial Nutrient [alpha]-Lipoic Acid on Improving Age-Associated Mitochondrial and Cognitive Dysfunction: Overview", *Neurochemical Research*, vol. 33, published online Jun. 29, 2007, (2008), pp. 194-203.

Long, Jiangang, et al., "D-Galactose toxicity in mice is associated with mitochondrial dysfunction: protecting effects of mitochondrial nutrient R-alpha-lipoic acid", *Biogerontology*, vol. 8, No. 3, (Feb. 14, 2007), pp. 373-381.

Murase, Takatoshi, et al., "Green tea extract improves running endurance in mice by stimulating lipid utilization during exercise", *Am J Physiol Regul Integr Comp Physiol*, vol. 290, No. 6, (Jan. 12, 2006), pp. R1150-R1156.

Park, Sang-Kyu, et al., "Gene Expression Profiling of Aging in Multiple Mouse Strains: Identification of Aging Biomarkers and Impact of Dietary Antioxidants", *Aging Cell*, vol. 8, No. 4, (Aug. 2009), pp. 484-495.

Prasad, Kedar N., "Intervention with Multiple Micronutrients Including Dietary and Endogenous Antioxidants for Healthy Aging", *Aging and Age-Related Disorders*, Eds. S. Bondy and K. Maise, Humana Press, (Jan. 1, 2010), pp. 55-78.

Ross, J. M., et al., "Natural substances counteract prematurely aging phenotypes in mtDNA mutator mice", *Abstracts of the Meeting of the Society for Neuroscience*, vol. 41, (Nov. 13, 2011), p. 120.09.

Saad, F., et al., "Dehydroepiandrosterone Treatment in the Aging Male—What Should the Urologist Know?", *European Urology*, vol. 48, No. 5, (2005), pp. 724-733.

Santos, R. S., "Beneficial effects of long-term administration of cholecalciferol on blood pressure and life-span of SHRSP rats", *European Journal of Neurology*, vol. 15, Suppl. 3, (Aug. 2008), p. 265.

Takatsu, Hirokatsu, et al., "Effect of Vitamin E on Learning and Memory Deficit in Aged Rats", *J Nutr Sci Vitaminol*, vol. 55, (2009), pp. 389-393.

Yasuhara, Takao, et al., "Dietary Supplementation Exerts Neuroprotective Effects in Ischemic Stroke Model", *Rejuvenation Research*, vol. 11, No. 1, (Mar. 1, 2008), pp. 201-214.

Invitation to Pay Additional Fees and Partial International Search Report mailed Dec. 17, 2014, PTC Appln. No. PCT/US2014/060510, 8 pages.

Alarcon De La Lastra, Catalina, et al., "Resveratrol as an anti-inflammatory and anti-aging agent: Mechanisms and clincal implications", *Molecular Nutrition & Food Research*, vol. 49, No. 5, (May 1, 2005), pp. 405-430.

Banji, David, et al., "Curcumin and piperine abrogate liquid and protein oxidation induced by D-galactose in rat brain", *Brain Research*, vol. 1545, (Apr. 6, 2013), pp. 1-11.

Banji, David, et al., "Piperine and curcumin exhibit synergism in attenuating D-galactose inducesd senescence in rats", *European Journal of Pharmacology*, vol. 703, No. 1-3, (Mar. 1, 2013), pp. 91-99.

Davis, J. M., et al., "Quercetin increases brain and muscle mitochondrial biogenesis and exercise tolerance", *Am J Physiol Regul Integr Comp Physiol*, vol. 296, No. 4, (Apr. 2009), pp. R1071-R1077.

Fu, Chunwang, et al., "Metabonomics study of the protective effects of green tea polyphenols on aging rats induced by D-galactose", *Journal of Pharmaceutical and Biomedical Analysis*, vol. 55, No. 5, (Mar. 5, 2011), pp. 1067-1074.

He, Miao, et al., "Protective effects of (−)-epigallocatechin-3-gallate on D-galactose-induced neuronal apoptosis in mice", *Neural Regeneration Research*, Retrieved via Internet: http://d.g.wanfangdata.com.cn/Periodical_zgsjzsyj-e200912007.aspx on Nov. 19, 2014, (Dec. 2009), 4 pages.

Jalili, Thunder, et al., "A mixture of grape seed & skin extract, green tea extract, resveratrol, and quercetin reduces blood pressure in hypertensive subjects with metabolic syndrome", *Database Biosis*, Database Accession No. PREV20130070554 abstract & FASEB Journal, vol. 24, Conference on Experimental Biology, Anaheim, CA, USA, (Apr. 2010), 2 pages.

Sun, Su W., et al., "Quercetin attenuates spontaneous behavior and spatial memory impairment in D-galactose-treated mice by increasing brain antioxidant capacity", *Nutrition Research*, vol. 27, No. 3, (Mar. 23, 2007), pp. 169-175.

Yao, Yu, et al., "Research on resveratrol's mechanism of immunity in anti-aging", *Medline Database, US National Library of Medicine*, Database Accession No. NLM16981461 abstract, & Zhong Yao Cai, Journal of Chinese Medicinal Materials, vol. 29, No. 5, (May 2005), pp. 464-467.

NUTRIENT COMBINATIONS FOR AFFECTING AN AGING PROCESS

CROSS-REFERENCE TO RELATED APPLICATION

This application is a non-provisional claiming priority to U.S. Provisional Patent Application No. 61/890,839, filed Oct. 14, 2013 and incorporated herein by reference.

BACKGROUND

D-galactose (D-gal), a physiological nutrient derived from lactose in milk, is metabolized in animals by D-galactokinase and galactose-1-phosphate uridyltransferase. Research has shown that D-gal treated animals showed some hallmarks of aging, such as a shortened life span, cognitive dysfunction, presbycusis, increased oxidative stress, decreased antioxidant enzyme activity, diminished immune responses, increased advanced glycation endproducts (AGEs), accumulation of mitochondrial DNA (mtDNA) mutations, and mitochondrial dysfunction.

Mitochondria are not only the major sites of intracellular reactive oxygen species (ROS) production, but also targets of ROS. This ROS-induced oxidative damage contributes to mitochondrial dysfunction, which in turn produces more ROS. This vicious cycle of ROS production and oxidative damage in the mitochondria suggests that mitochondrial dysfunction plays an important role in the aging process.

SUMMARY

The instant invention provides several nutrient combinations found to have beneficial effects on the aging process. In particular, the effects of the nutrient combinations in a mouse model of aging (i.e. D-gal exposed mice) were evaluated and studied with respect to cognitive dysfunction, locomotor activity, mitochondrial dysfunction, gene expression and lifespan. Based on the evaluation, it was found that three combinations of nutrients effectively reversed D-gal-induced muscular impairment, reversed complex I dysfunction in both skeletal muscle and heart muscle and/or attenuated the skeletal muscle impairment by improving mitochondrial function.

In one embodiment, the nutrient combination is a composition including an effective amount of a combination of nutrients sufficient to affect mitochondrial function. Representatively, the nutrients may be mitochondria targeting antioxidants and cofactors, which are referred to herein as "mitochondrial nutrients". Representative mitochondrial nutrients may include, but are not limited to, resveratrol, grape seed extract, quercetin, pterostilbene, fisetin, black tea (theaflavins), ubiquinol CoQ10, R-lipoic acid, acetyl-L-carnitine, pyrroloquinoline quinone (PQQ), tocopherols, tocotrienols (mixed), Vitamin D3 (cholecalciferol), green tea extract (98% polyphenols, 45% epigallocatechin gallate (EGCG)), and dehydroepiandrosterone (DHEA).

In another embodiment, a method of affecting an aging process in a subject is provided. The method may include administering to a subject an effective amount of a combination of mitochondrial nutrients sufficient to affect an aging process. The effect on the aging process may include, but is not limited to, attenuating skeletal muscular impairment, reversing complex I dysfunction, reversing a mitochondrial dysfunction caused by the aging process, increasing a lifespan of the subject as compared to a control subject, and regulating genes in a manner similar to that found in caloric restriction (CR).

In another embodiment, a method of identifying a combination of mitochondrial nutrients sufficient to affect an aging process in a subject is disclosed. The method may include administering a combination of mitochondrial nutrients to a subject and determining whether the mitochondrial nutrients affect an aging process in the subject. Determining may include performing a strength test to determine whether the combination of mitochondrial nutrients attenuates skeletal muscle impairment caused by an aging process. Determining may also include performing a gene expression analysis to determine whether the combination of mitochondrial nutrients results in a gene expression profile consistent with a gene expression profile for CR or evaluating a lifespan of the subject to determine whether a median, a mean or a maximum lifespan of the subject is increased with respect to a control subject.

BRIEF DESCRIPTION OF THE DRAWINGS

The embodiments disclosed herein are illustrated by way of example and not by way of limitation in the figures of the accompanying drawings in which like references indicate similar elements. It should be noted that references to "an" or "one" embodiment in this disclosure are not necessarily to the same embodiment, and they mean at least one.

DETAILED DESCRIPTION

Figure 1A:
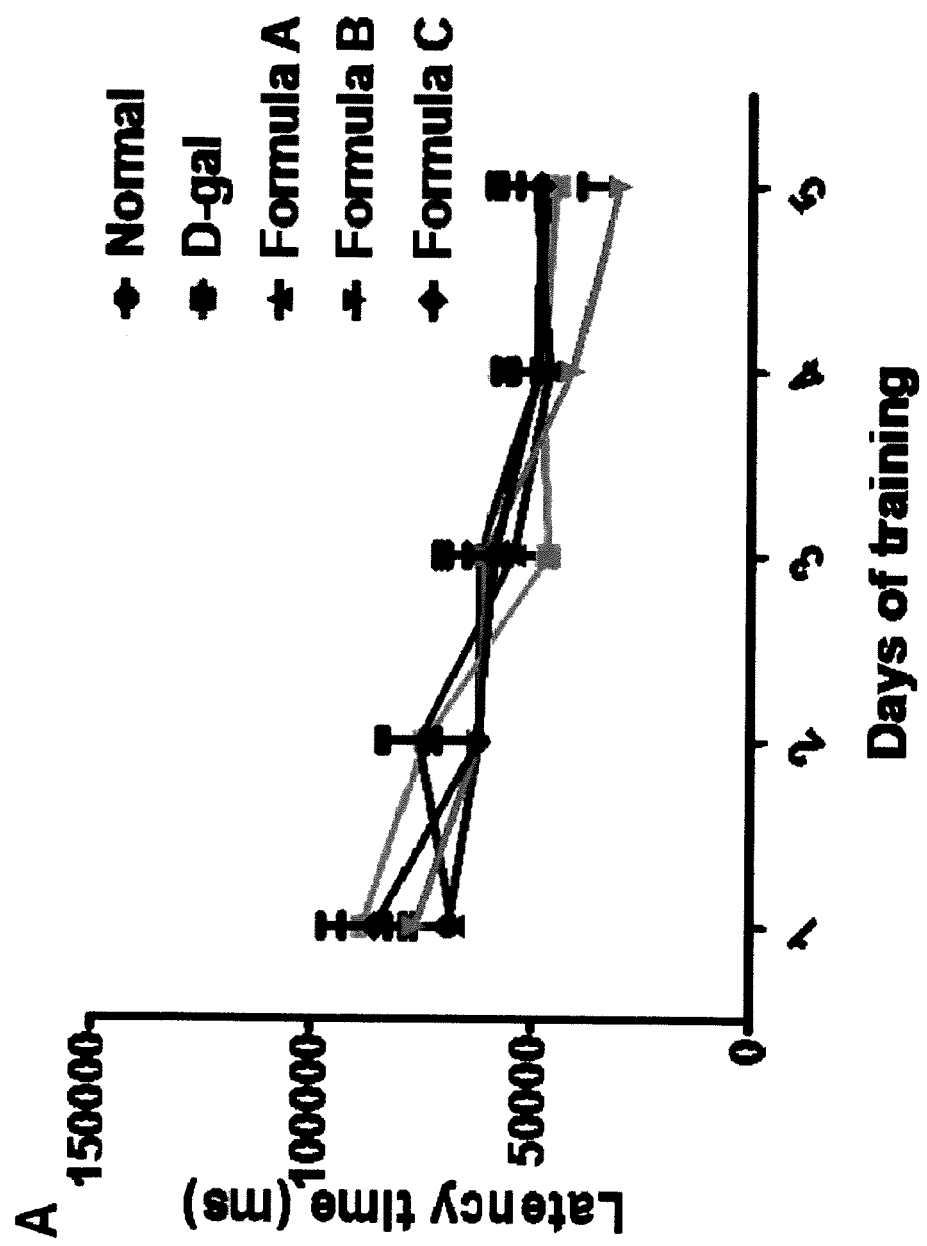
FIG. 1A illustrates the results of a spatial memory test with the Morris Water Maze (MWM) with respect to latency time.

The instant invention describes a group of mitochondria targeting antioxidants and cofactors, which are referred to herein as "mitochondrial nutrients". The administration of these mitochondrial nutrients to a subject is shown herein to effectively reverse the mitochondrial dysfunction that occurs during the aging process. In addition, the synergistic beneficial effects of combinations of these mitochondrial nutrients are demonstrated herein to be even more powerful than administration of a single mitochondrial nutrient alone in promoting mitochondrial function. In this aspect, a synergistic amount of the mitochondrial nutrients may be combined such that the therapeutic effects of the mitochondrial nutrients when administered in combination is greater than their effect when administered alone. Representatively, three formulations including different combinations of the mitochondrial nutrients are shown herein to rescue mitochondrial dysfunction. Additionally, the combinations of mitochondrial nutrients are shown to relieve one or more disorders associated with the aging process. Representative mitochondrial nutrients may include, but are not limited to, resveratrol, grape seed extract, quercetin, pterostilbene, fisetin, black tea (theaflavins), ubiquinol CoQ10, R-lipoic acid, acetyl-L-carnitine, pyrroloquinoline quinone (PQQ), tocopherols, tocotrienols (mixed), Vitamin D3 (cholecalciferol), green tea extract (98% polyphenols, 45% epigallocatechin gallate (EGCG)), and dehydroepiandrosterone (DHEA).

The specific combinations of mitochondrial nutrients are referred to herein generally as "Formulations" or "Formulas" and more specifically as "Formula A", "Formula B" or "Formula C." Formula A is designed to inhibit tumorigenesis. Formula A may, for example, include one or more of the following mitochondrial nutrients: resveratrol, grape seed extract, quercetin, pterostilbene, fisetin, and black tea (theaflavins). Formula A may include any one or more of the mitochondrial nutrients in a synergistic amount found sufficient to have a beneficial effect on the aging process and associated disorders or conditions in a subject, for example, an amount sufficient to inhibit tumorigenesis. Representatively, Formula A may include from about 20 mg to about 260 mg, for example from about 100 mg to about 180 mg, more specifically, from about 130 mg to 150 mg of resveratrol; from about 20 mg to about 160 mg, for example from about 40 mg to about 140 mg, for example, from 70 mg to 110 mg grape seed extract; from about 60 mg to about 500 mg, for example from about 150 mg to about 400 mg, for example, from 200 mg to 300 mg of quercetin; from about 4 mg to about 20 mg, for example from about 8 mg to about 16 mg, for example, from 10 mg to 14 mg of pterostilbene; from about 30 mg to about 50 mg, for example from about 35 mg to about 45 mg, for example, from 38 mg to 42 mg of fisetin; and from about 300 mg to about 450 mg, for example from about 350 mg to about 400 mg, for example, from 370 mg to 380 mg of black tea.

Formula B is designed to target mitochondrial metabolic deregulation. Formula B may, for example, include one or more of the following mitochondrial nutrients: ubiquinol CoQ10, R-lipoic acid, acetyl-L-carnitine, pyrroloquinoline quinone (PQQ), tocopherols, and tocotrienols (mixed). Formula B may include any one or more of the mitochondrial nutrients in a synergistic amount found sufficient to have a beneficial effect on the aging process and associated disorders or conditions in a subject, for example, an amount sufficient to cause mitochondrial metabolic deregulation. Representatively, Formula B may include from about 50 mg to about 150 mg, for example from about 75 mg to about 125 mg, more specifically, from 100 mg to 110 mg of ubiquinol CoQ10; from about 150 mg to about 300 mg, for example from about 175 mg to about 275 mg, more specifically, from 200 mg to 250 mg of R-lipoic acid; from about 370 mg to about 2000 mg, for example from about 750 mg to about 1050 mg, more specifically, from of 1000 mg to 1025 mg of acetyl-L-carnitine; from about 10 mg to about 20 mg, for example from about 12 mg to about 18 mg, more specifically, from 14 mg to 16 mg of PQQ; from about 325 mg to about 375 mg, for example from about 330 mg to about 370 mg, more specifically, from 350 mg to 360 mg of tocopherols; and from about 50 mg to about 150 mg, for example from about 75 mg to about 125 mg, more specifically, from 90 mg to 110 mg of tocotrienols.

Finally, Formula C is designed to target mitochondrial related steroid degeneration. Formula C may, for example, include one or more of the following mitochondrial nutrients: Vitamin D3 (cholecalciferol), green tea extract (98% polyphenols, 45% epigallocatechin gallate (EGCG)), and dehydroepiandrosterone (DHEA). Formula C may include any one or more of the mitochondrial nutrients in a synergistic amount found sufficient to have a beneficial effect on the aging process and associated disorders or conditions in a subject, for example, an amount sufficient to target mitochondrial related steroid degeneration. Representatively, Formula C may include from about 100 IU to about 7000 IU, for example from about 2500 IU to about 5500 IU, more specifically, from 3500 IU to 4500 IU of Vitamin D3; from about 25 mg to about 730 mg, for example from about 250 mg to about 550 mg, more specifically, from 350 mg to 450 mg of green tea extract; and from about 15 mg to about 200 mg, for example from about 75 mg to about 140 mg, more specifically, from 100 mg to 120 mg of DHEA.

Representatively, Example 1 illustrates one embodiment of exemplary amounts of the mitochondrial nutrients that may be included in one or more of Formula A, Formula B and Formula C. Other formulations, having more or less mitochondrial nutrients in varying amounts are further contemplated. All amounts are listed in mg per kg of body weight of the subject or mg per 60 kg of body weight of the subject, except where otherwise noted, and include amounts used in the Experiments provided herein (identified under the "Concentration" column) and their human equivalents (identified under the "Human Eqv" column).

Example 1

| Ingredient | Concentration (mg/kg) | Human Equv (mg/60 kg) |
| --- | --- | --- |
| Trans-resveratrol | 51.4 | 250 |
| Grape seed extract | 30.8 | 150 |
| Quercetin | 12.5 | 61 |
| Prerostilbene | 4.0 | 19 |
| Fisetin | 9.9 | 48 |
| Black Tea (Theaflavins) | 90.4 | 440 |
| CoQ10 | 20.6 | 100 |
| R-Lipoic acid | 30.8 | 150 |
| Acetyl-L-carnitine | 150.0 | 730 |
| PQQ | 3.0 | 15 |
| Tocopherols (mixed) | 73.8 | 359 |
| Tocotrienols (mixed) | 29.8 | 145 |

-continued

| Ingredient | Concentration (mg/kg) | Human Equv (mg/60 kg) |
|---|---|---|
| D3 IU/kg (cholecalciferol) | 400.00 (IU/kg) | 1946 (IU/60 kg) |
| Green tea extract (98% polyphenols, 45% EGCG) | 149.0 | 725 |
| DHEA | 10.0 | 49 |

In still further embodiments, exemplary mitochondrial nutrient combinations and amounts found to have a synergistic or additive effect on an aging process of a subject are provided in Examples 2-4. In particular, Examples 2-4 illustrate the effective amounts (as a concentration in mg per kg of body weight of the subject) and dose ranges (in mg) of each of the mitochondrial ingredients of Formulas A-C effective for affecting an aging process in a human subject as described herein. The dose ranges represent, for example, the effective amount of the mitochondrial nutrient that may be included in a single dose of the Formula that may be administered to the human subject on a daily basis. It should be understood that Example 2 corresponds to Formula A, Example 3 corresponds to Formula B and Example 4 corresponds to Formula C.

Example 2

Formula A

| Ingredient | Concentration (mg/kg) | Dose Range (mg) |
|---|---|---|
| Trans-resveratrol | 0.33-4.33 | 20-260 |
| Grape seed extract | 0.33-2.67 | 20-160 |
| Quercetin | 1.0-8.33 | 60-500 |
| Prerostilbene | 0.07-0.33 | 4-20 |
| Fisetin | 0.50-0.83 | 30-50 |
| Black Tea (Theaflavins) | 5.0-7.50 | 300-450 |

Example 3

Formula B

| Ingredient | Concentration (mg/kg) | Dose Range (mg) |
|---|---|---|
| CoQ10 | 0.83-2.50 | 50-150 |
| R-Lipoic acid | 2.50-5.00 | 150-300 |
| Acetyl-L-carnitine | 6.17-33.33 | 370-2000 |
| PQQ | 0.17-0.33 | 10-20 |
| Tocopherols (mixed) | 5.42-6.25 | 325-375 |
| Tocotrienols (mixed) | 0.83-2.50 | 50-150 |

Example 4

Formula C

| Ingredient | Concentration (mg/kg) | Dose Range (mg) |
|---|---|---|
| D3 IU/kg (cholecalciferol) | 1.67-116.67 (IU/kg) | 100-7000 (IU/kg) |
| Green tea extract (98% polyphenols, 45% EGCG) | 0.42-12.17 | 25-730 |
| DHEA | 0.25-3.33 | 15-200 |

In one embodiment, the mitochondrial nutrient(s) Formulation (i.e. Formula A, Formula B or Formula C) is administered to a mammal in the form of a composition. The composition may include a combination of mitochondrial nutrients (i.e. Formulas A-C) and a vehicle. The composition may be administered to the mammal by any technique suitable for introducing the mitochondrial nutrient combination to the mammal. Representatively, the composition may be administered via an oral, intravenous, rectal, transmucosal, intestinal, parenteral, intrathecal, intraventricular, intraperitoneal, transdermal, subcutaneous capsular dispersion (implant), intranasal or intraocular administration route. The vehicle may be, for example, saline or any other similarly suitable fluid, or any other suitable medium for facilitating administration of the treatment agent to the mammal via injection or some other means. Alternatively, the composition may be suitable for oral administration in a solid or liquid form and may further include excipients such as sugars or cellulose preparations and colorants.

The composition may be formed by mixing an amount of the mitochondrial nutrient combination with a vehicle until a concentration of the mitochondrial nutrient effective for having a beneficial impact on the aging process or aging related disorders or conditions (e.g. inhibiting tumorigenesis, targeting mitochondrial metabolic deregulation, targeting mitochondrial related steroid degeneration, reversing D-gal-induced muscular impairment, reversing complex I dysfunction, improving mitochondrial function, etc.) is reached.

The composition may be administered by any of the above routes pursuant to a regimen for administering the composition which provides a beneficial effect on the aging process and aging related disorders or conditions. Representatively, the composition may be administered to the mammal periodically. In some embodiments the composition is administered to the mammal once a day. In other embodiments, the composition is administered to the mammal once a day or more. For example, the composition may be administered twice daily or once a week or once a month. It is contemplated that the frequency and duration of administration of the composition may vary depending upon the amount of treatment agent in the composition and the desired effects.

In some embodiments, the composition is in the form of a pill, a capsule, a tablet, or a lozenge. The composition may further be administered in the form of a powder, cream, liquid, spray or ointment. In other embodiments, the composition is administered in the form of an aqueous solution. In some embodiments, a mitochondrial nutrient formulation in the form of a powder or aqueous solution may be incorporated into a candy bar, food bar, power bar, nutrition bars/gels, sports and energy drinks and shots, along with substances typically used in those items, such as grains, fruits, flavorings, nuts, binders, etc. In still further embodiments, the composition is administered in the form of an implant implanted within the mammal which releases a desired amount of the treatment agent over time. It is contemplated that the form of the composition may vary depending upon the desired administration route. Representatively, where the composition is to be injected into the tissue of the mammal, the composition may be in the form of an aqueous solution.

In some embodiments, a release rate of the mitochondrial nutrient(s) into the mammalian system may be controlled. In some embodiments, an enteric coating, a pH dependent polymer, a polymer in a matrix, or a delayed release coating may be used to control a release rate of the mitochondrial nutrient(s) within the system. In some embodiments, the delayed release coating may be used to make delayed release pills, either as a component of the matrix in which the mitochondrial nutrient(s) is mixed or as a coating on the outside of the pill or capsule. The coatings may allow for a slow or sustained or extended release of the mitochondrial nutrient(s). For example, significant quantities of the mitochondrial nutrient(s) may be released for absorption into the blood stream over specific timed intervals, for example over an extended period, such as 12 hours or longer, e.g. 12-24 hours, after ingestion. For some formulations, extended release (ER) components can also be referred to as sustained release (SR) or prolonged release (PR). In some embodiments, the coatings allow for immediate-release or periodic-release of the mitochondrial nutrient(s). In this aspect, the mitochondrial nutrient(s) may be released substantially immediately upon contact with gastric juices and will result in substantially complete dissolution within, for example, about 1 hour. Immediate release (IR) components can also be referred to as instant release. It is contemplated that the immediate release coating may be any conventional coating suitable for allowing for release of the treatment agent within about 1 to 2 hours. It is further contemplated that any type of release controlling coating and technique conventionally known may be utilized as deemed desirable for controlling a release rate of the treatment agent.

Various combinations of mitochondrial nutrients, for example, Formulas A-C were tested on groups of subjects to evaluate their ability to affect the aging process. In particular, the cognitive function and locomotor activity in D-gal exposed mice that were administered Formulas A-C which were examined in Experiment I. The D-galactose (D-gal) induced aging model was used to investigate cognitive dysfunction, locomotor activity, and mitochondrial dysfunction involved in D-gal exposure in mice. The results showed that D-gal exposure (125 mg/kg/d, 8 weeks) resulted in a serious impairment in grip strength in mice, whereas spatial memory and locomotor coordination remained intact. Interestingly, muscular mitochondrial complex I deficiency occurred in the skeletal muscle of mice exposed to D-gal. Mitochondrial ultra-structure abnormality was implicated as a contributing factor in D-gal-induced muscle impairment. In Experiment I, it was found that Formulas A-C effectively reversed D-gal-induced muscular impairment and Formulas B and C were especially effective in reversing complex I dysfunction in both skeletal muscle and heart muscle. These findings show that: 1) chronic exposure to D-gal results in specific muscular impairment in mice, rather than causing general, premature aging; 2) poor skeletal muscle strength induced by D-gal may be due to the mitochondrial dysfunction caused by complex I deficiency; and 3) Formulas A-C attenuated the skeletal muscle impairment, for example, by improving mitochondrial function.

Gene expression studies were also performed to analyze the ability of each of Formulations A-C to serve as a caloric restriction mimetic (CRM). Caloric restriction (CR) refers to a technique in which subjects, such as mice or humans, are fed a diet ("a CR diet") which has less than a "normal" amount of calories for a certain period of time. Typically, the amount of food given in the CR diet is less than about 50% or 40% of the minimum recommended daily amount measured in calories. The effects of a CR diet have been extensively studied, and numerous researchers have developed techniques to screen for interventions, such as therapeutic substances or compounds, which when administered to a subject on a normal diet tend to cause the subject's physiological or biological state to mimic the state of an organism on a CR diet. Such interventions are referred to as CR mimetics because they cause the biological state of the organism receiving the intervention to mimic the state of a similar organism on a CR diet even if the organism is not on a CR diet. The ability of each of Formulations A-C to serve as a CRM is described in Experiment II.

Finally, the data from the differential gene expression profiling, comparative analysis and pathway assessment of the CRM candidates was used to perform a lifespan study. In particular, the data from the mitochondrial study and gene expression profile suggested that one or more of Formulations A-C may be involved in metabolism and energy balance which may be connected to the increase of lifespan associated with CR. Based on the mitochondrial biogenesis data and bioinformatics data, Formulas B and C in particular were selected for the lifespan studies. The results of the lifespan study are described in Experiment III.

It is further to be understood that although the experimental results herein are described in connection with a rodent model of aging, such model is widely recognized and widely used as the most physiologically representative experimental model for human aging. In this aspect, it is contemplated that the effects of the formulations disclosed herein on aging in the rodent model may further be achieved in humans.

The results of Experiments I-III will now be described in detail.

Experiment I

In this study, the cognitive function and locomotor activity in D-gal exposed mice administered Formulas A-C was evaluated. In addition, mitochondrial impairment and the effects of Formulas A-C on the mitochondrial dysfunction induced by D-gal was evaluated.

Behavioral Tests in D-Gal Exposed Mice

Figure 1B:
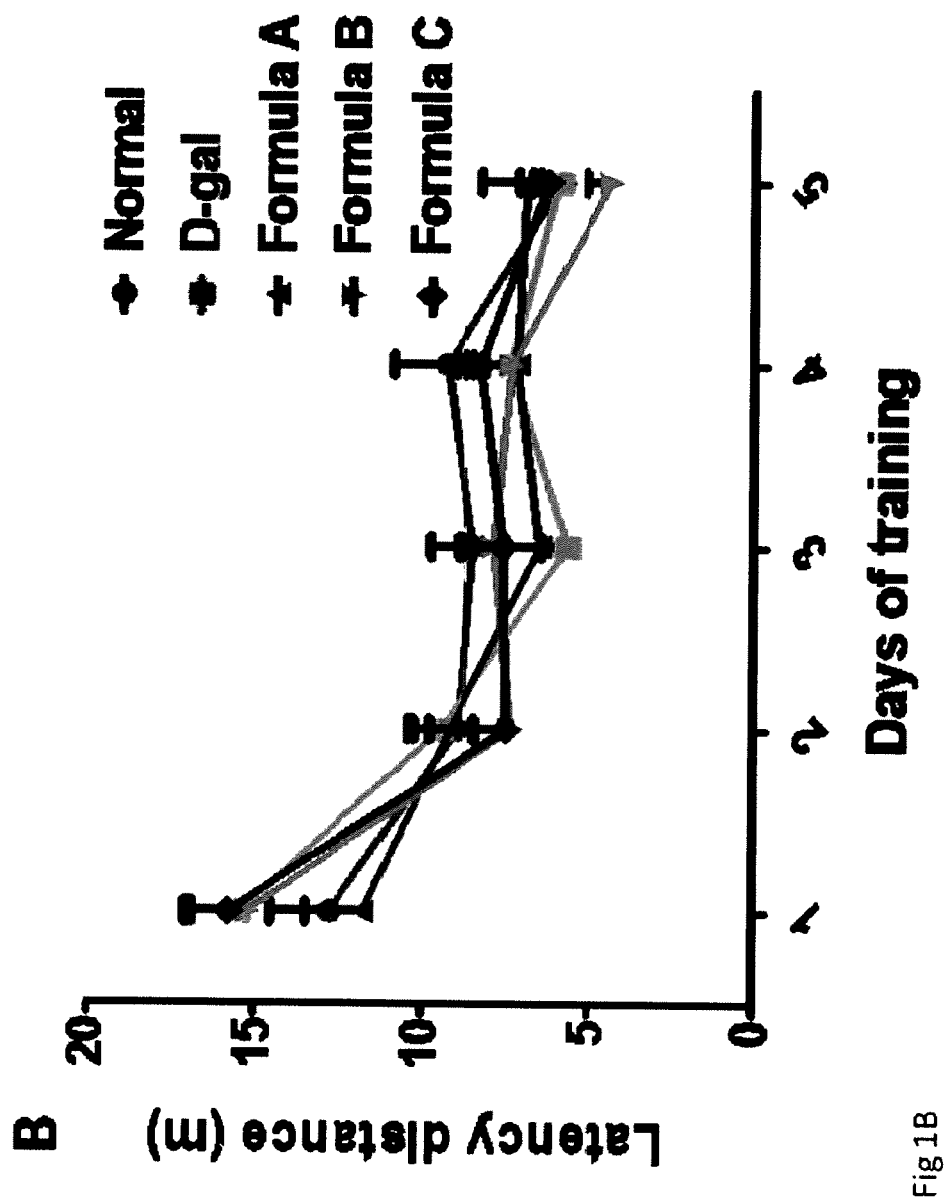
FIG. 1B illustrates the results of a spatial memory test with the Morris Water Maze (MWM) with respect to latency distance.

The Morris Walter Maze (MWM) was applied to measure cognitive deficiencies in D-gal exposed mice. It was found that 8-weeks of D-gal exposure did not affect the escape latency or swimming distance of mice in the MWM compared to the normal control. In particular, FIG. 1A illustrates the latency time for finding a platform of control subjects, D-gal subjects and subjects administered Formulas A-C over a period of training days. The subjects, in this case, were mice. Values are illustrated as mean±SEM of 12 animals. As can be seen in FIG. 1A, no significant difference of latency time and distance was found between control and D-gal exposure mice. In addition, FIG. 1B illustrates the latency distance to the platform of control subjects, D-gal subjects and subjects administered Formulas A-C over the same period of training days as illustrated in FIG. 1A. No significant difference of latency distance was found between control and D-gal exposure mice. Additionally, the administration of nutrient combinations in the D-gal mice did not cause any alteration in the spatial memory compared to the D-gal group.

Figure 2:
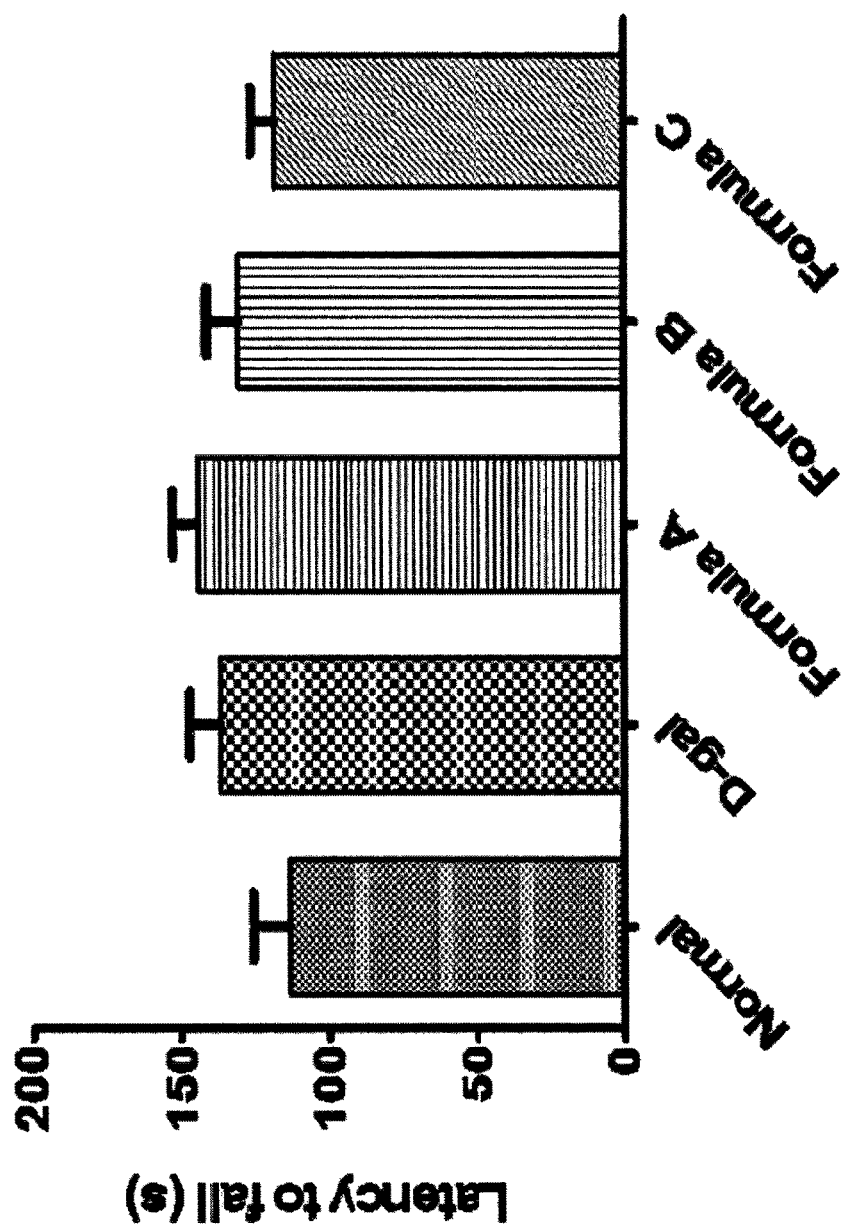
FIG. 2 illustrates a coordination test with the Rota-Rod.

FIG. 2 illustrates a coordination test with the Rota-Rod. In addition, latency to fall was tested. Values are mean±SEM of 12 animals. No difference in latency time was found between control and D-gal exposure mice. Similarly, the motor coordination detected with the Rota-Rod test showed no changes between the control, D-gal, Formula A, Formula B and Formula C groups of subjects.

Figure 3:
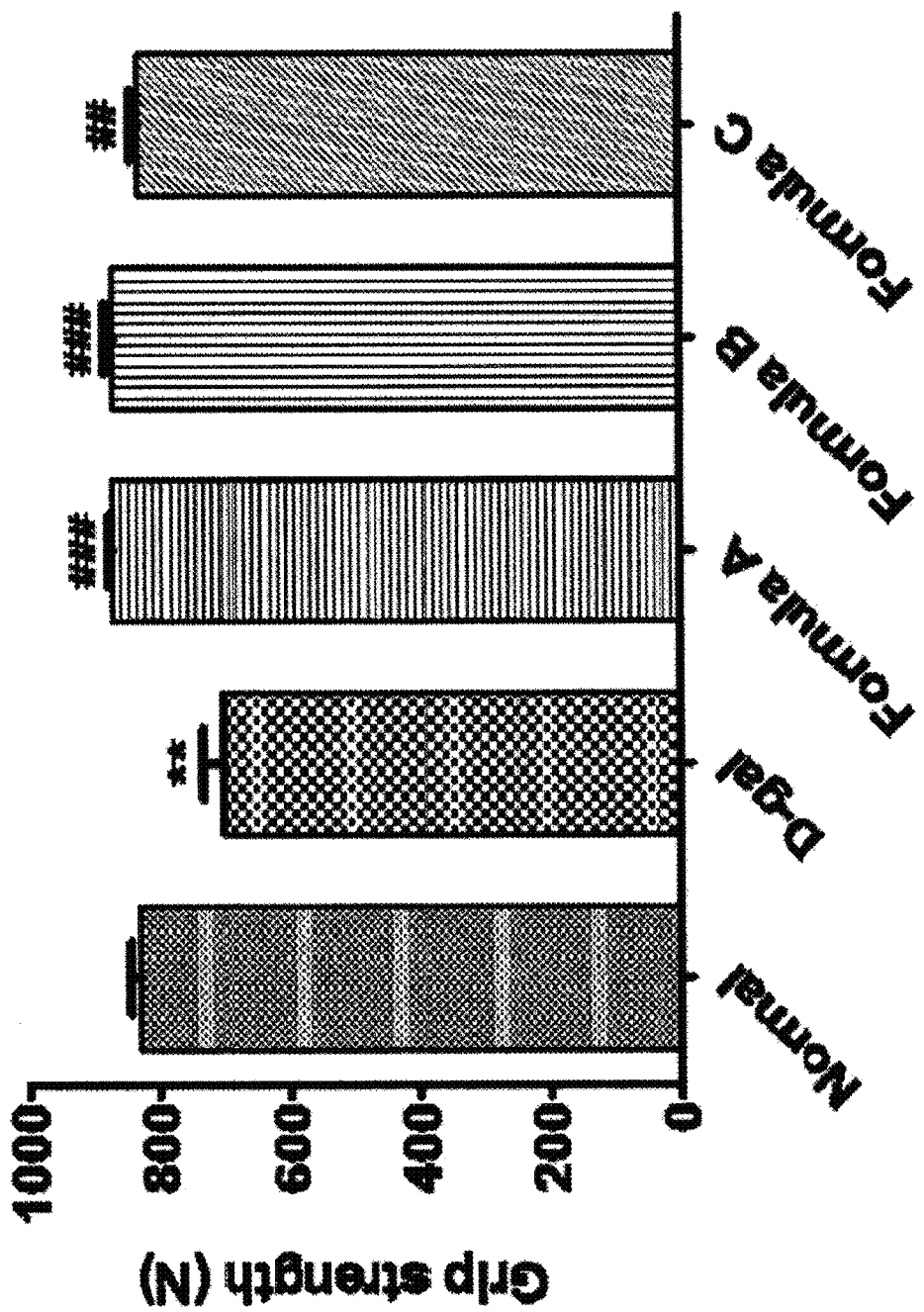
FIG. 3 illustrates the results of a grip strength test.

It should further be understood that a decrease in strength is a reliable indicator of the aging process. In this aspect, the rodent grip strength test is a putative measure of muscular strength and has been previously used to screen for neuromuscular function. FIG. 3 illustrates the results of a grip strength test. In particular, grip strength of forelimb was tested. Values are means±SEM of 12 mice. **$P<0.01$ versus Normal group, ##$P<0.01$ versus D-gal group, ###$P<0.001$ versus D-gal group. FIG. 3 shows that D-gal treated mice exhibited significantly weaker grip strength than mice in the control group (t-test, n=12; P<0.01), suggesting that D-gal induces skeletal muscle strength impairment in mice. In addition, FIG. 3 shows that nutrient Formulas A, B, and C efficiently restored muscle strength to levels similar to that of the control group.

Ultra-Structure of the Mitochondria in Muscle

Figures 4A, 4B, 4C, 4D, 4E:
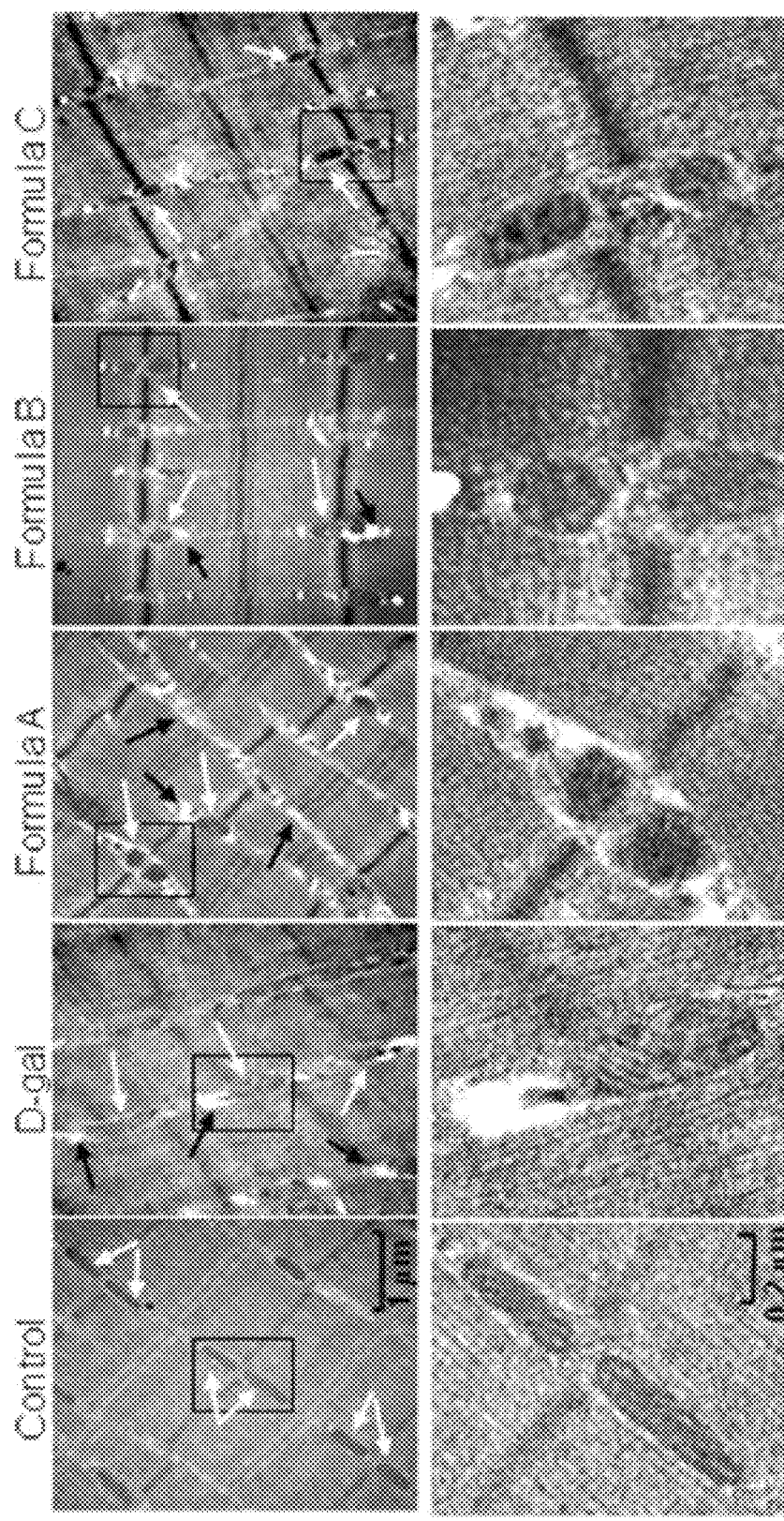
FIG. 4A illustrates electron microscopy results with respect to the gastrocnemius muscle of a control subject.
FIG. 4B illustrates electron microscopy results with respect to the gastrocnemius muscle of a D-gal subject.
FIG. 4C illustrates electron microscopy results with respect to the gastrocnemius muscle of a subject administered a nutrient formulation according to one embodiment.
FIG. 4D illustrates electron microscopy results with respect to the gastrocnemius muscle of a subject administered a nutrient formulation according to another embodiment.
FIG. 4E illustrates electron microscopy results with respect to the gastrocnemius muscle of a subject administered a nutrient formulation according to another embodiment.

To understand the grip strength loss caused by D-gal exposure, the morphology of mice gastrocnemius muscles were further evaluated with transmission electron microscopy. FIGS. 4A-4E illustrate the transmission electron microscopy results of the gastrocnemius muscle. In particular, FIG. 4A illustrates the transmission electron microscopy for the control group of subjects (i.e. mice), FIG. 4B illustrates the transmission electron microscopy for the D-gal group, FIG. 4C illustrates the transmission electron microscopy for the Formula A group, FIG. 4D illustrates the transmission electron microscopy for the Formula B group, FIG. 4E illustrates the transmission electron microscopy for the Formula C group. A magnified view of the upper panels in FIGS. 4A-4E are shown in the lower panels.

As can be seen from FIGS. 4A-4E, D-gal treated mice had a broader range of mitochondria sizes than the normal control group, and an increased number of vacuoles and swollen and/or poorly formed mitochondria were present in the D-gal treated group compared to the normal control group. It can further be seen from FIGS. 4A-4E that all of Formulas A-C partially reversed the aberrant mitochondria induced by D-gal, and Formula C additionally reduced the formation of vacuoles. White arrows indicate mitochondria and black arrows indicate vacuoles.

In addition, in the control group as illustrated by FIG. 4A, long rows of mitochondria with similar rod-like shape and size were regularly aligned in pairs between myofibrils. In contrast, swollen and elongated mitochondria with obvious cristae disruption appeared in D-gal treated mice, as illustrated in FIG. 4B. In addition, more vacuoles, along with the distorted mitochondria, were observed in mice treated with D-gal compared to control mice.

There were varied effects on the morphology of the mitochondria of mice treated with Formulas A-C. Representatively, mitochondria of mice treated with Formula A or Formula B, as illustrated by FIGS. 4C and 4D respectively, remained broken and contained vacuoles, although the size of the mitochondria was smaller than in mice treated with D-gal alone. The aberrant morphology of mitochondria following D-gal exposure was greatly ameliorated for mice treated with Formula C. In particular, as illustrated in FIG. 4E, mitochondria were nearly intact with less vacuoles present following the treatment with Formula C.

These results show that D-gal exposure results in a remarkable mitochondrial morphology distortion in skeletal muscle. In addition, the results show that nutrient Formulas A-C, especially Formula C, effectively ameliorated the mitochondrial morphology impairment in gastrocnemius muscle induced by D-gal.

Mitochondrial Complex & Dehydrogenase Activities

In view of the abnormal mitochondrial morphology in the skeletal muscle of the D-gal treated mice, the activities of some key enzymes in the electron transport chain (ETC) and the tricarboxylic acid (TCA) cycle were further examined. Among ETC complexes I, II, and IV, α-KGDH and PDH, it was found that only complex I activity was impaired in the gastrocnemius muscle of D-gal-treated mice (n=7; P<0.05).

Figure 5:
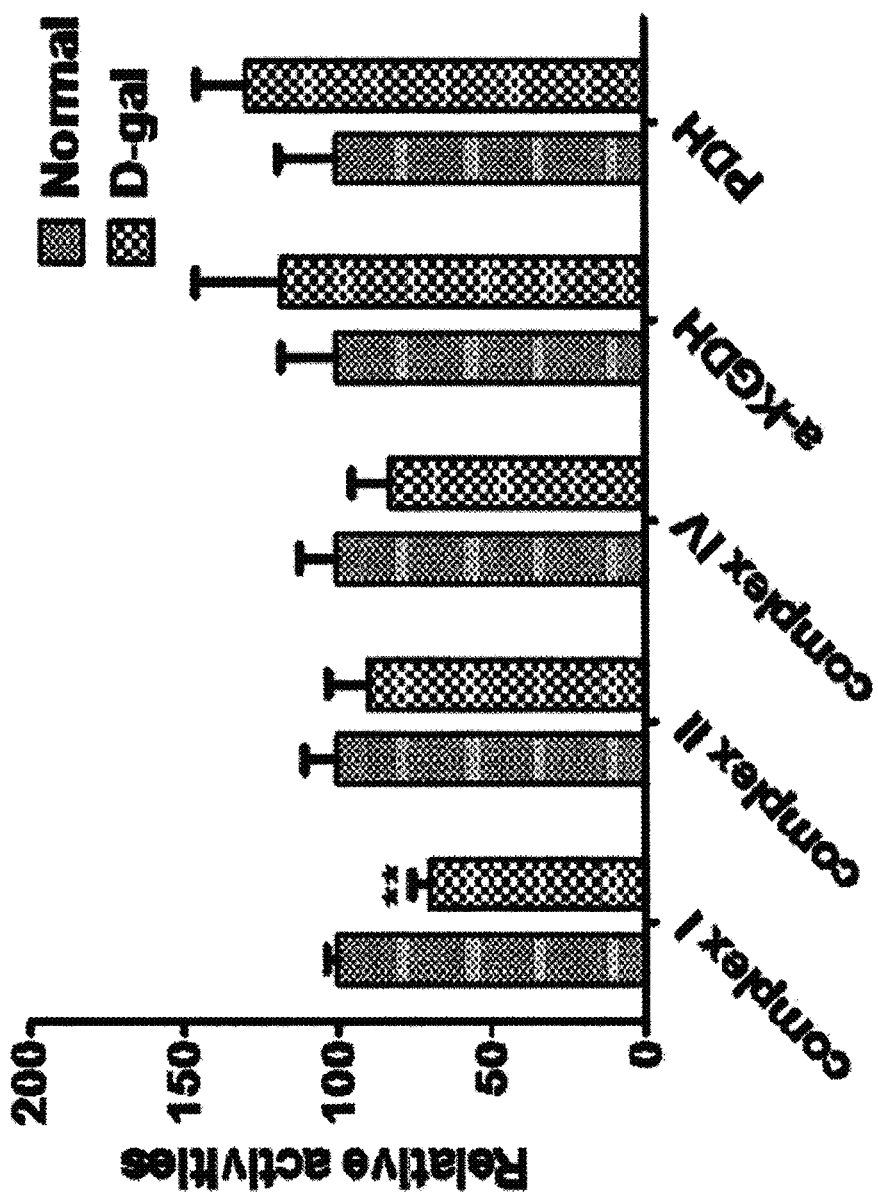
FIG. 5 illustrates activities of complex I, II, IV, α-KGDH and PDH in gastrocnemius mitochondria.

FIG. 5 illustrates activities of complex I, II, IV, α-KGDH and PDH in gastrocnemius mitochondria. Representatively, as can be understood from FIG. 5, chronic D-gal treatment induced complex I specific impairment in gastrocnemius mitochondria. Values are means±SEM of 12 mice. **P<0.01 versus Normal group.

Figure 6:
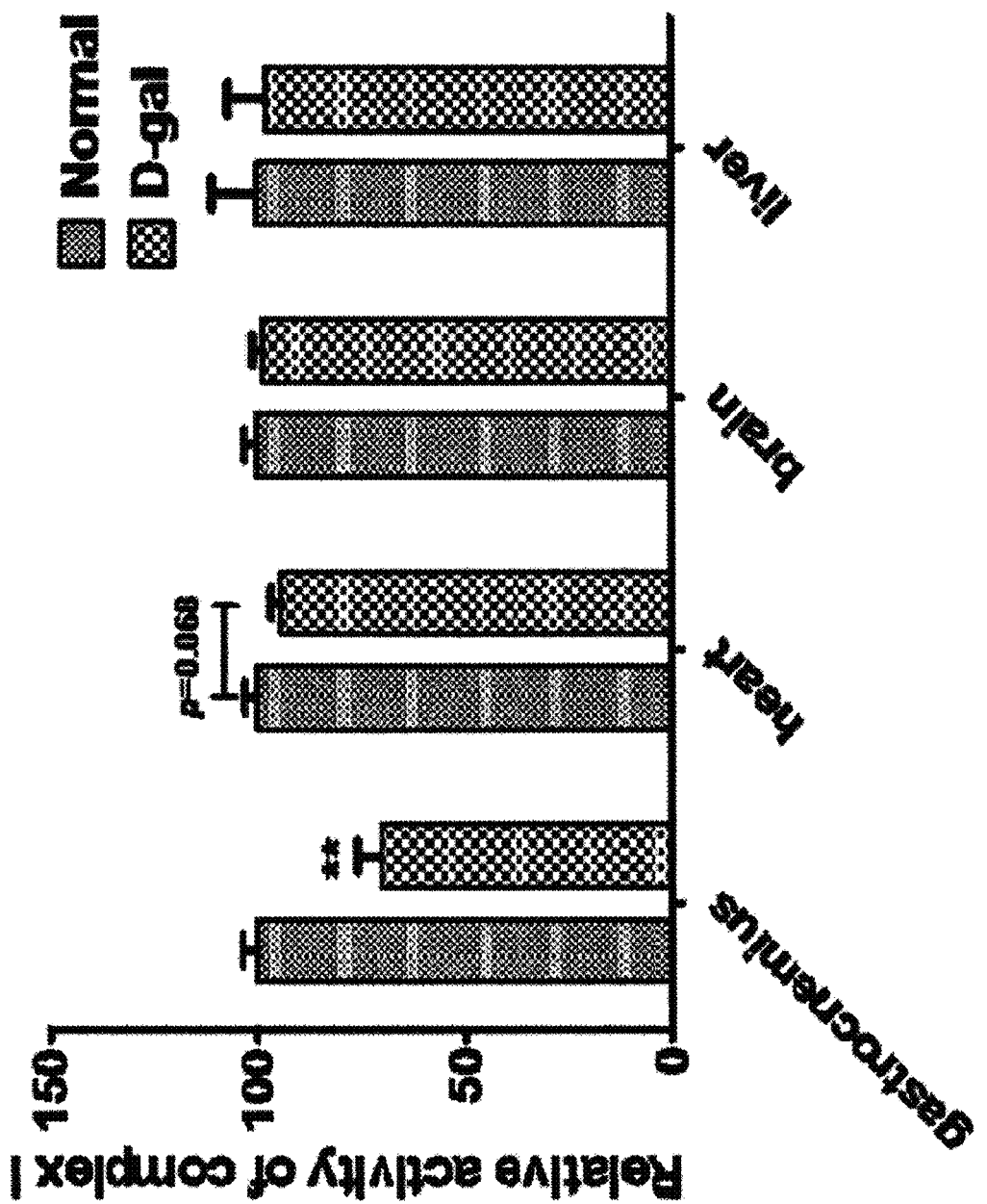
FIG. 6 illustrates activities of complex I in mitochondria from multiple tissues.

The activity of complex I was also assayed in several other tissues, such as liver, heart, and brain. FIG. 6 illustrates activities of complex I in mitochondria from multiple tissues. As is illustrated by the results shown in FIG. 6, D-gal administration impairs the activity of complex I in gastrocnemius. Values are means±SEM of 12 mice in gastroanemius, 11 mice in heart and 12 mice in brain and liver. **P<0.01 versus Normal group. In addition, the results shown in FIG. 6 demonstrate that complex I activity is decreased specifically in skeletal muscle, with a marginal decrease in heart muscle, compared to the control mice.

Figure 7:
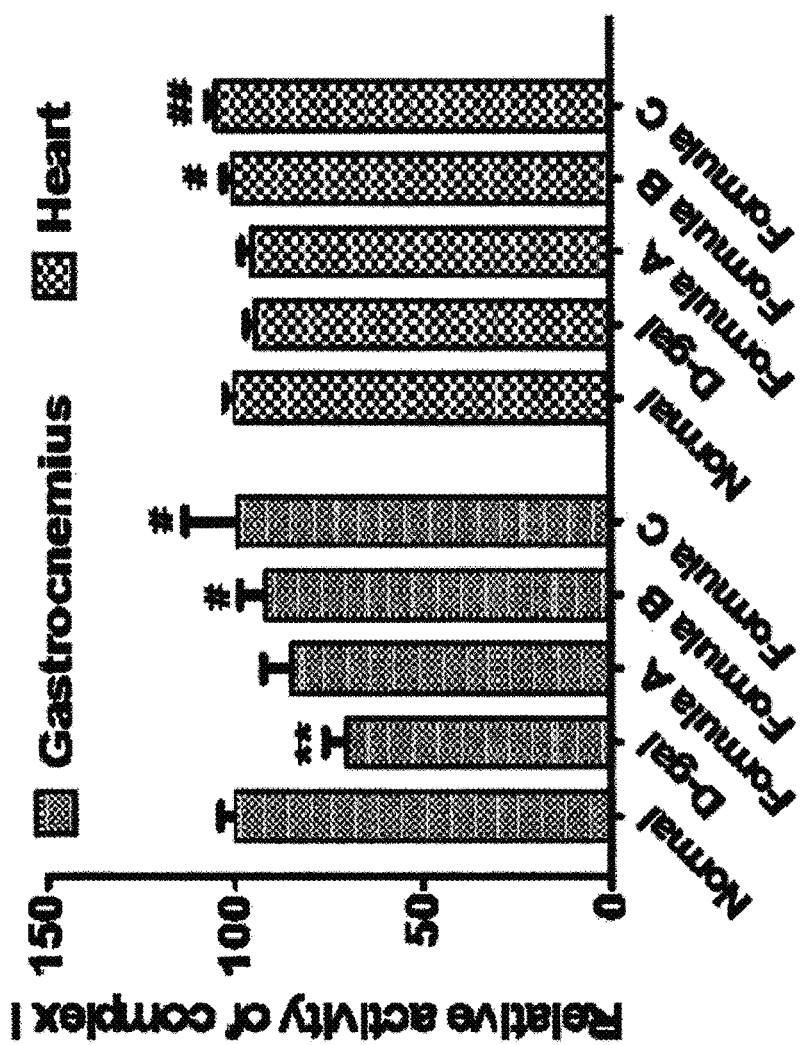
FIG. 7 illustrates the effects of nutrient formulas on the activity of complex I in gastrocnemius and heart mitochondria.

FIG. 7 illustrates the effects of Formulas A-C on the activity of complex I in gastrocnemius and heart mitochondria. Activities of complex I of gastrocnemius (n=12) and heart (n=11) in all groups were assayed. All values are expressed as means±SEM. **P<0.01 versus Normal group, #P<0.05 versus D-gal group, ##P<0.01 versus D-gal group. The results show that Formula B and C, and to some extent Formula A, successfully promoted complex I activity following D-gal treatment in skeletal muscle and in heart muscle.

D-Gal Induced a Muscle Specific Impairment and Mitochondrial Complex I Deficiency.

Aging is associated with a progressive loss of muscle mass and strength, a condition known as sarcopenia. Poor muscular strength is highly predictive of disability and mortality, and often results in the loss of independent living, thereby affecting an individual's quality of life. As a putative and direct measurement of muscular strength, the grip strength test has been used to screen for neuromuscular function. In the grip strength test of Experiment I, the results of which are illustrated in FIG. 3, it was found that D-gal treated mice possessed significantly weaker grip strength when compared with the control group.

In addition, it is understood that aging is associated with a significant decline in mitochondrial function. Furthermore, as a key regulator of apoptosis and ATP production, mitochondrial dysfunction has emerged as a critical player in the onset and progression of sarcopenia. Experiment I illustrates that the mitochondria in the gastrocnemius muscle exhibited a markedly abnormal morphology characterized by an increase in the heterogeneity of mitochondria size, an impairment in mitochondrial integrity, an increase in the number of vacuoles, and a swelling of the mitochondria in mice treated with D-gal (see FIGS. 4A-4E). The abnormal morphology suggests that poor muscular strength induced by D-gal might be tightly associated with mitochondrial decay.

It is well known that energy production through oxidative phosphorylation occurs in mitochondria and is catalyzed by successive enzyme complexes. PDH and α-KGDH in the TCA cycle catalyze reactions producing reduced nicotinamide adenine dinucleotide (NADH), the most important electron donor for the ETC. The electron transfer chain consists of mitochondrial complexes I, II, and IV as the initial and terminal electron acceptors in electron transfer chain. Therefore, as previously discussed, in Experiment I, the activity of these key mitochondrial enzymes were measured and it was found that complex I activity was significantly depressed in D-gal mice (see FIG. 5). Among the tissues investigated, the complex I activity was depressed in skeletal muscle and marginally depressed in heart, but not in the liver and brain as illustrated by FIG. 6. In galactose-1-phosphate uridyltransferase (GALT) deficient mice, dietary galactose is abnormally metabolized to galactitol, which is a similar condition as in D-gal overloaded mice. Galactitol has been found to accumulate in heart and skeletal muscle other than liver, brain, and kidney in GALT deficient mice, whereas accumulated galactitol can lead to osmotic stress and ROS production. Therefore, the muscle specific damage found in Experiment 1 is believed to be caused by galactitol accumulation.

Since complex I is the major site of physiological and pathological ROS production, it was determined that decreased complex I activity enhanced ROS production, which in turn induced mitochondrial fragmentation or other morphology distortion as seen in Experiment I.

Nutrient Formulas Effectively Rescued Mitochondrial Dysfunction Induced by D-Gal.

Since mitochondrial dysfunction is considered to play a major role in the aging process, Formulas A-C were designed to ameliorate mitochondrial dysfunction. The synergistic and beneficial effects on mitochondrial function for all the mitochondrial nutrients of each of Formulas A-C were studied. Based on the studies and the experimental results herein, the mitochondrial nutrients were assigned to groups of mitochondrial nutrients having different beneficial effects as previously described. The combinations of mitochondrial nutrients described herein were found to have synergistic effects in various metabolic pathways and to be more potent than treating the mammals with individual nutrients alone. For example, supplementing mice with R-lipoic acid, acetyl-L-carnitine, and CoQ10 has a more significant beneficial effect on age-related oxidative stress than individual treatment with these compounds. Therefore, the mitochondrial nutrients combined in the Formulas disclosed herein, in particular Formulas A-C, were specifically selected based on their synergistic effects when combined and their effects on mitochondrial impairment induced by D-gal exposure in mice were assessed.

Overall, Experiment I demonstrates that chronic systemic exposure to D-gal causes muscle impairment and mitochondrial complex I deficiency. Interestingly, the mitochondrial nutrient Formulas A-C disclosed herein were found to at least partially restore mitochondrial morphology and complex I activity, and rescue the loss in grip strength induced by D-gal.

As previously discussed, gene expression studies were also performed to analyze the ability of each of the Formulas to serve as a CRM. The ability of each of Formulas A-C to serve as a CRM are described in Experiment II.

Experiment II

Samples A, B and C, which were taken from subjects administered Formula A, Formula B and Formula C, respectively, and a control group were analyzed using the R version 2.15 and Bioconductor version 2.10. The CR data and the respective control data from the BMP data base were reanalyzed with the same version before comparative analysis.

QC Report

QC parameters were determined using affyQCRport. The 20 CEL files for samples A, B, and C showed very high correlations within the sample (A, B and control 0.935-0.96 and C 0.92-0.96).

In comparison, the correlations for CR were ranging from 0.86 to 0.94 with 12 CEL files showing correlations of 0.9-0.94, and the remaining CEL with each other and with the first 12 showing only 0.86-0.91. The CR matched controls showed overall correlations of 0.76-0.92 with 8 showing the best correlations among each other of 0.88-0.92.

All QC parameters for samples A, B, C and their matched control were very uniform across all 20 CEL files for each sample.

Differential Expression Profiles

Differential expression between the samples and their respective controls was calculated using Bioconductor packages affy and limma. The resulting differential expression profiles were then compared, calculating correlations (Pearson product moment correlation coefficient), counts of up or down regulated probesets, common up or down regulated probesets, global distributions of M-values and p-values.

Correlations

The correlation of expression profiles for a sample using different number of CEL files was further examined. For samples A, B, and C these correlations were high. Moreover, the best correlations between CR and the tested samples were observed with sample C whether overall probesets, probesets with M-value >|0.265| which corresponds to a >20% up or down regulation, or probesets with M-value >|1| which corresponds to a >100% up or down regulation.

Differential Expression

Table 1 summarizes the number of differentially expressed probes and Table 2 summarizes the number of differentially expressed genes.

TABLE 1

| probesets | $M \geq |1|, P \leq .05$ | | |
|---|---|---|---|
| | down | up | Total |
| 101/CR8CO8 | 78 | 54 | 132 |
| 101/CR12CO12 | 85 | 62 | 147 |
| 120/SA20CO20 | 105 | 12 | 117 |
| 120/SB20CO20 | 251 | 40 | 291 |
| 120/SC20CO20 | 13 | 13 | 26 |

TABLE 2

| genes | $M \geq |1|, P \leq .05$ | | |
|---|---|---|---|
| | down | up | Total |
| 101/CR8CO8 | 62 | 41 | 103 |
| 101/CR12CO12 | 67 | 49 | 116 |
| 120/SA20CO20 | 88 | 9 | 97 |
| 120/SB20CO20 | 201 | 28 | 229 |
| 120/SC20CO20 | 10 | 12 | 22 |

The count of probesets that are differentially expressed in both CR and samples A, B, or C are shown in Table 3, together with the percentage of all up or down regulated probesets for the sample and the number of probesets that are oppositely regulated compared to CR. Sample A, which showed negative correlation with CR, had the lowest percentage of common probesets, but inversely the highest percentage of oppositely regulated probesets. Sample C, on the other hand, had the highest percentage of probesets regulated in the same direction as CR and the lowest percentage of probesets inversely regulated than in CR. This is also reflected in the higher correlation between sample C and CR.

The count of up/down regulated genes in common with CR is shown in Table 4. As can be seen from Table 4, the count is larger than the probeset count as other probesets for the same gene can be differentially expressed. Sample C, again, shows the lowest number of genes with opposite differential expression.

TABLE 3

| M >= |.265|, P <= .01 | Probesets common differentially expressed with CR8CO8 (% of up/down regulated probesets) | | Probesets opposite differentially expressed than in CR8CO8 (% of total diff. expressed probesets) |
|---|---|---|---|
| | down | up | |
| SA20CO20 | 43 (3.7%) | 20 (5.9%) | 177 (11.8%) |
| SB20CO20 | 160 (8.8%) | 106 (11.3%) | 193 (7%) |
| SC20CO20 | 84 (12%) | 74 (14%) | 58 (4.7%) |

TABLE 4

| M >= |.265|, P <= .01 | Common differentially expressed genes with CR8CO8 | | Genes opposite differentially expressed than in CR8CO8 |
|---|---|---|---|
| | down | up | |
| SA20CO20 | 116 | 21 | 221 |
| SB20CO20 | 237 | 105 | 254 |
| SC20CO20 | 93 | 76 | 84 |

Pathway Analysis

For the pathway analysis the GO pathway annotation for all probesets were retrieved using the Bioconductor package mouse 4302.db and GO.db. To measure whether a pathway was over/under represented in the up/down regulated expression profile the ratio of observed to expected fraction of the probesets was calculated.

Genes of Interest

The probesets for the genes of interest were extracted for CR and samples A, B and C. Of the 384 probeset examined 12 were up-regulated (M-value>0.265) in sample C and 2 were down regulated, most of which were also up or down regulated in CR. The most noteworthy genes affected by these probesets are Ppargc1a and Ppargc1b (peroxisome proliferative activated receptor, gamma, coactivator 1 alpha and beta) and Foxo1 (forkhead box O1), which have several probeset up regulated in CR and sample C. For these probesets all annotated GO pathways were extracted.

Thus, it can be concluded based on the results of Experiment II that Formulas A-C, and particularly, Formula C, may also act as CRMs.

Example III

B6C3/F1 (C57BL/6XC3H) mice were randomly grouped into 60 mice for control, Formula B and Formula C treatments. The dosing for each group of animals started at the age of 12-months. The food consumption was recorded on a daily bases and the body weight for each animal was evaluated weekly.

Figure 8:
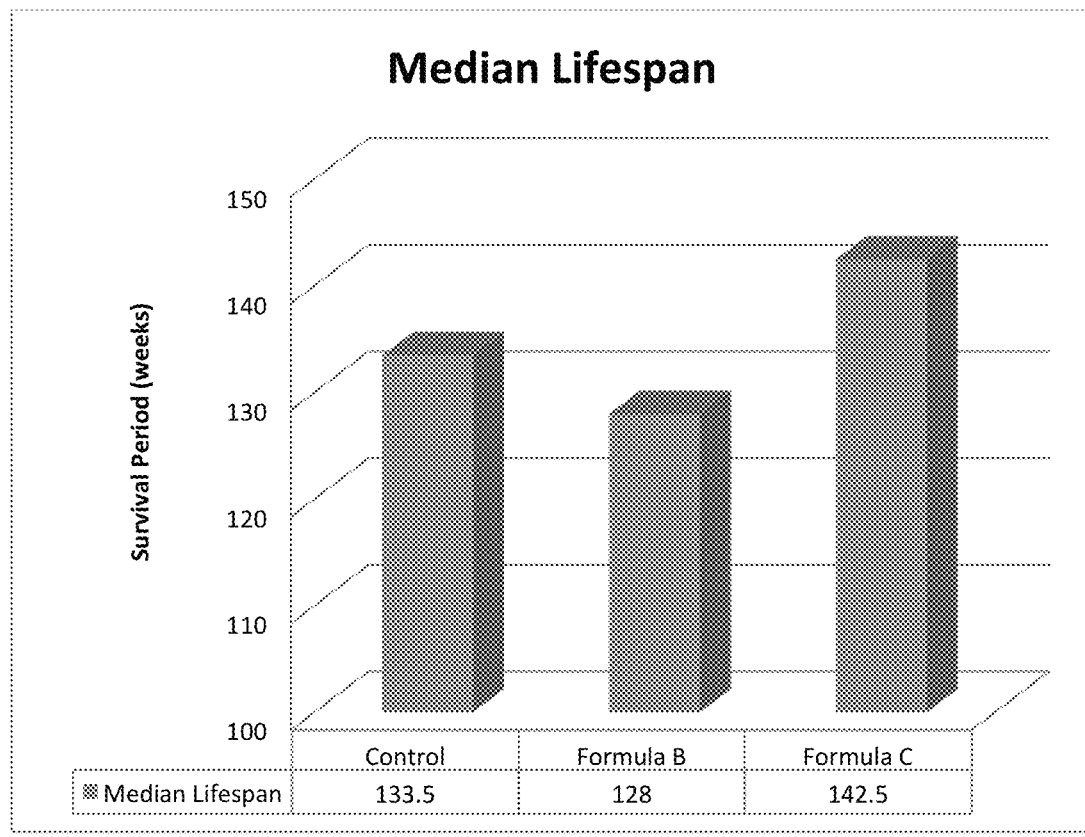
FIG. 8 illustrates the median lifespan of test subjects in a lifespan study.

As can be seen from FIG. 8, the median lifespan for the Control animals was 133.5 weeks, the Formula B treated group was 128 weeks, and the Formula C treated group was 142.5 weeks.

Figure 9:
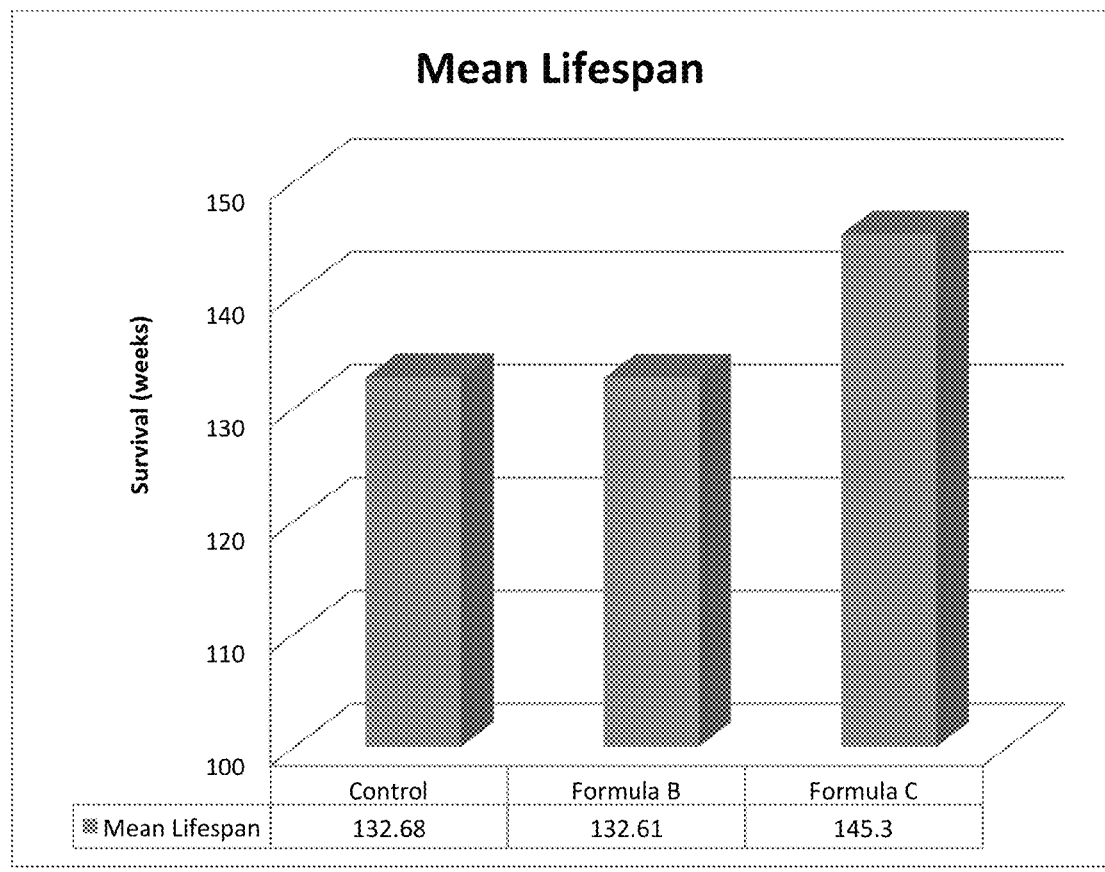
FIG. 9 illustrates the mean lifespan of test subjects in a lifespan study.

As can be seen from FIG. 9, the mean lifespan for the Control animals was 132.68 weeks, the Formula B treated was 132.61 weeks, and the Formula C treated was 145.3 weeks.

Figure 10:
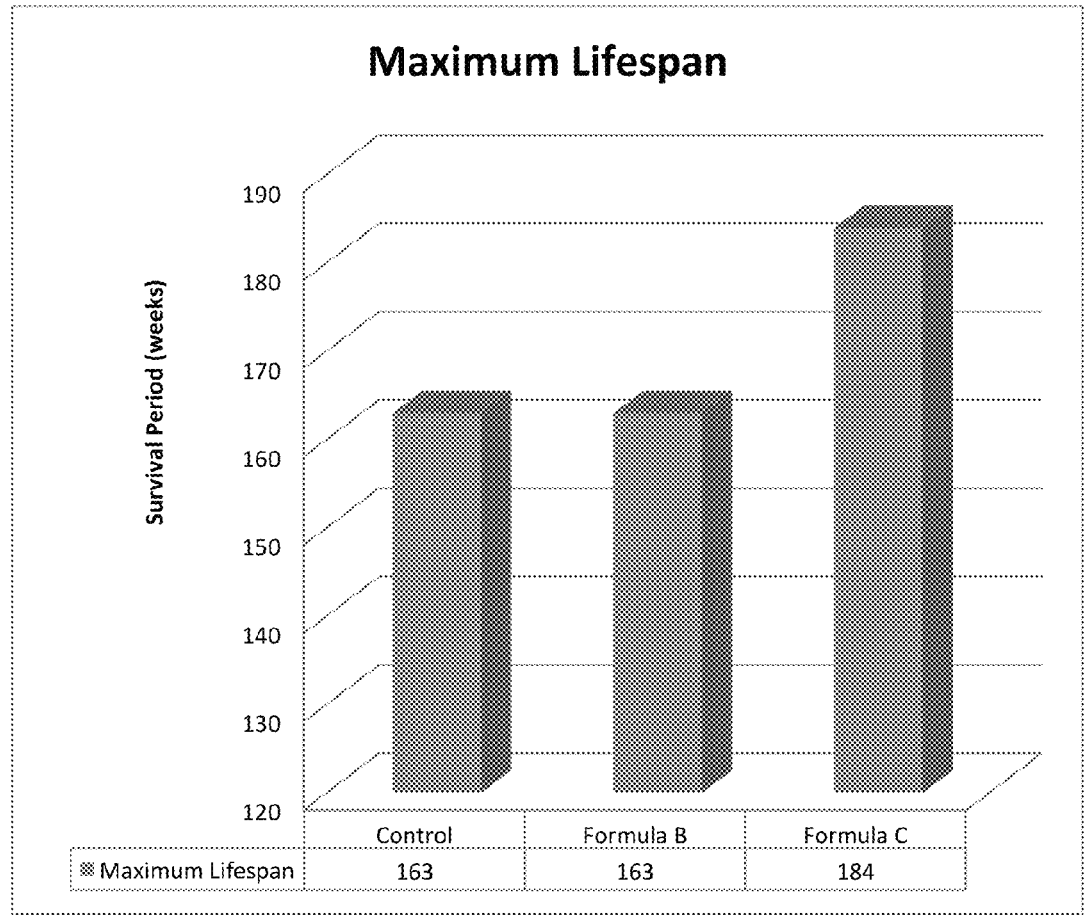
FIG. 10 illustrates the maximum lifespan of test subjects in a lifespan study.

Finally, as can be seen from FIG. 10, both the Control and Formula B groups reached 163 weeks maximum lifespan, and the Formula C treated group demonstrated 184 weeks maximum survival.

Figure 11:
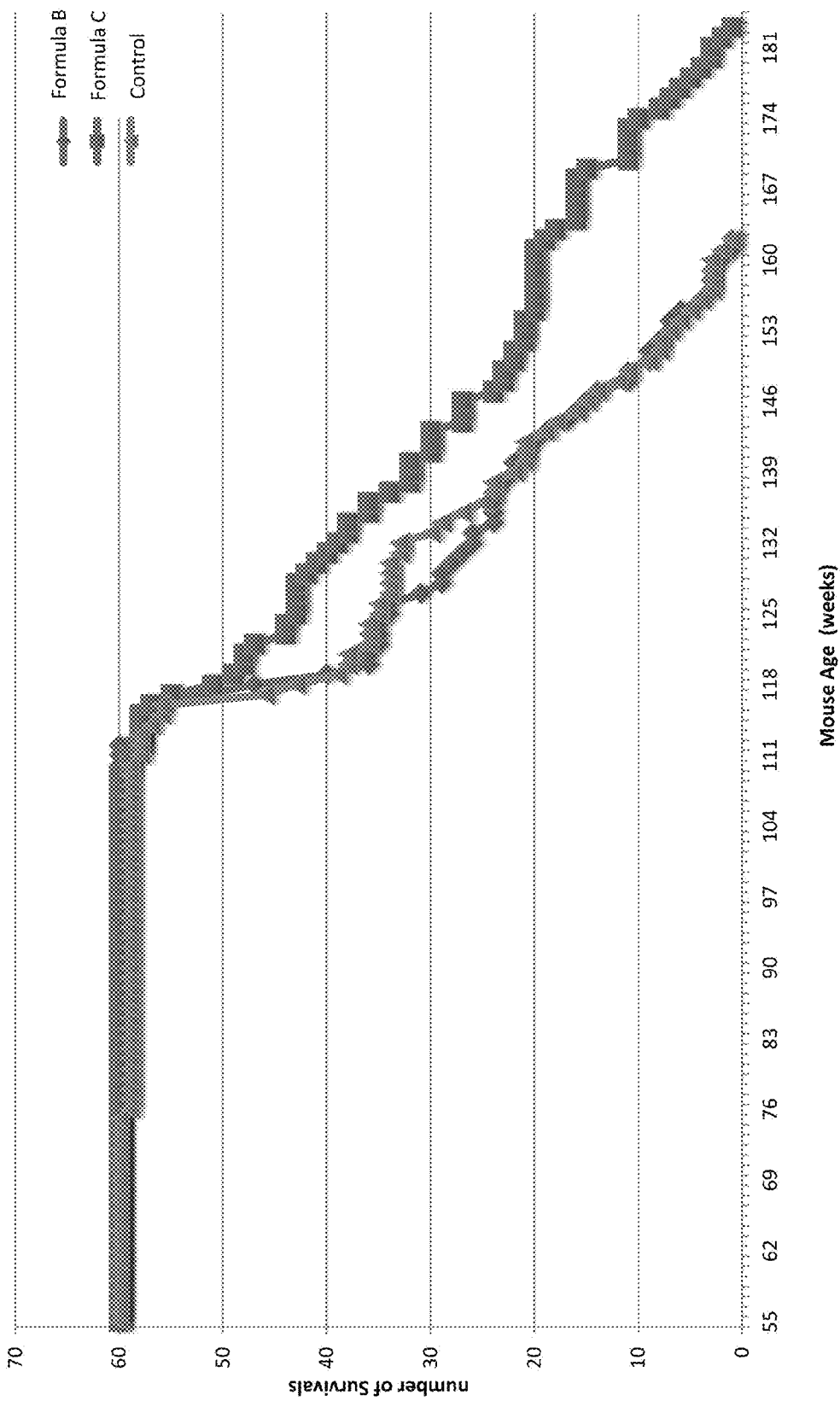
FIG. 11 illustrates the life expectancy of test subjects in a lifespan study.

FIG. 11 illustrates the life expectancy of the Control group, the Formula B group (p=0.98), and the Formula C group (p<0.0008). These results show that compared to the Control, the Formula C treatment demonstrated a 6.7% increase of median lifespan, 9.5% increase of mean lifespan and 12.9% increase of maximum survival rate.

Figure 12:
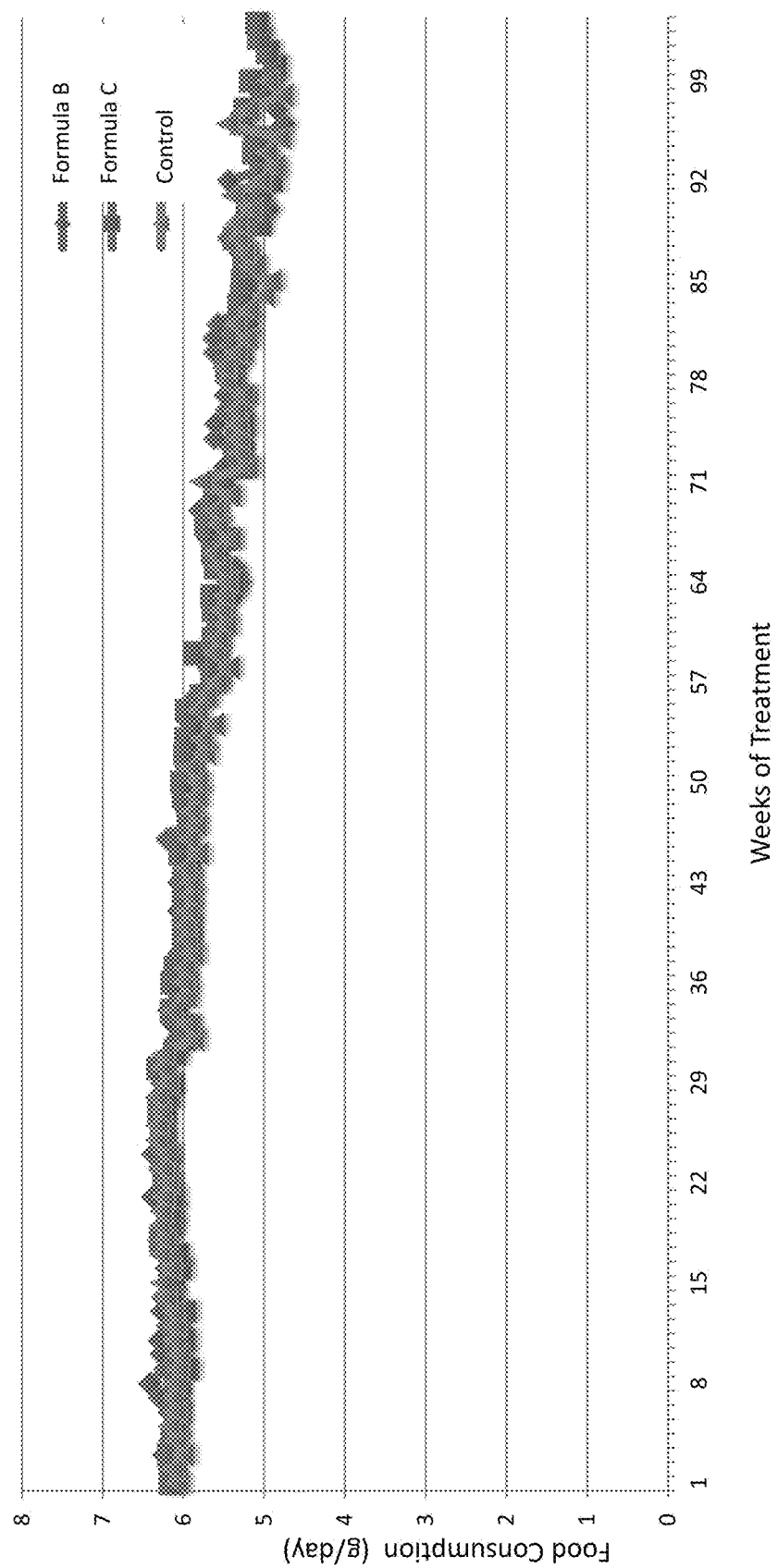
FIG. 12 illustrates the food consumption of test subjects in a lifespan study.

The food consumption of each group of rodents before and during their dosing stage was also analyzed. The results of the food consumption analysis are illustrated by FIG. 12. It was found that there was no significant difference between the groups treated with Formulas B and C and the Control animals.

Figure 13:
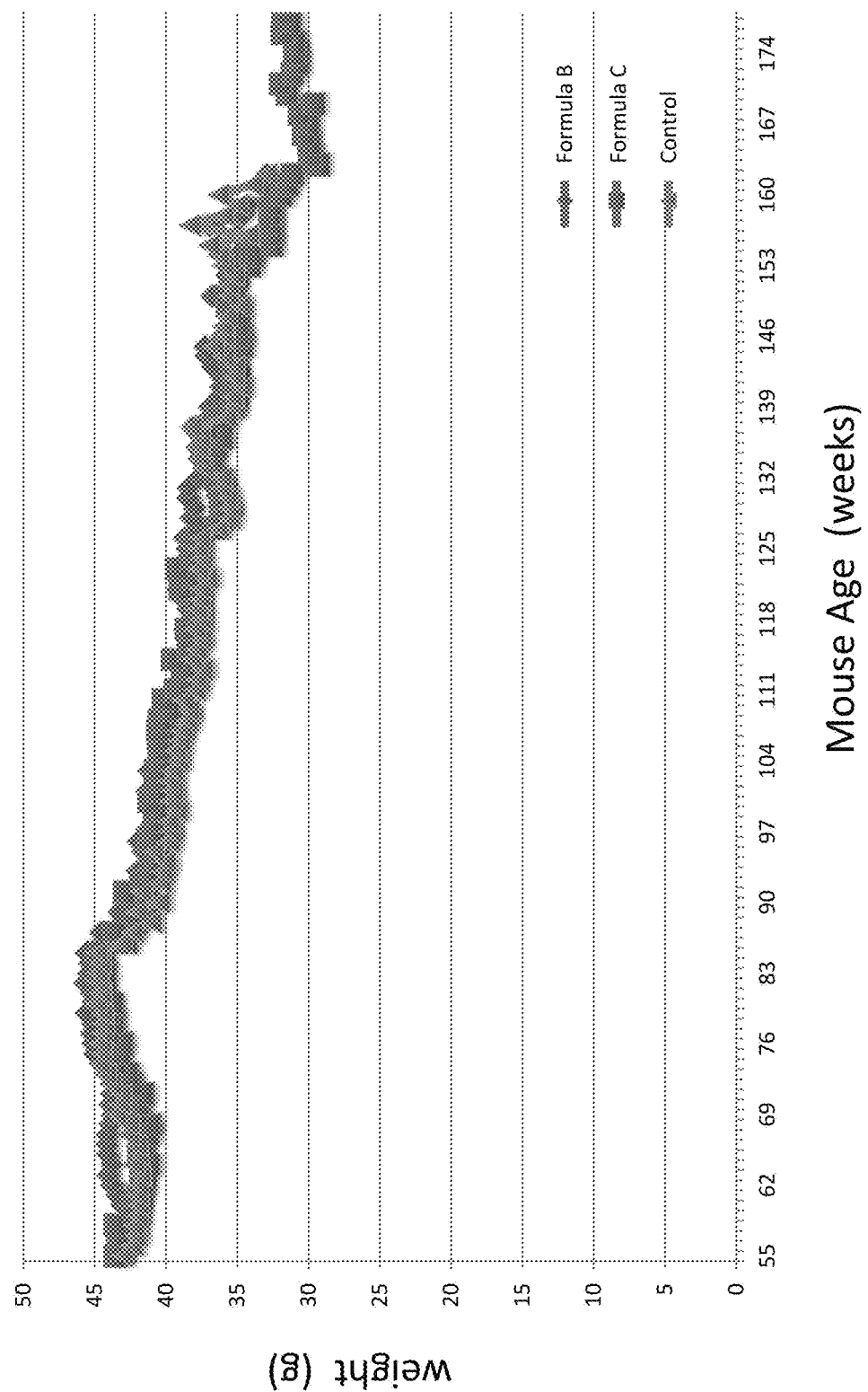
FIG. 13 illustrates the body weight of test subjects in a lifespan study.

The body weight of each animal was also evaluated and analyzed statistically. The results of the body weight analysis are illustrated by FIG. 13. It was found that there was no significant increase or decrease of the body weight among the groups.

In summary, among the three Formulas studies (e.g. Formulas A-C), all the formulas showed a beneficial effect on the aging process. Formula B and Formula C demonstrated the overlap expression of CR regulated genes compared to the CR gene expression profile. In addition, Formula B and Formula C were especially effective in reversing complex I dysfunction in both skeletal muscle and heart muscle. The beneficial properties of the Formula B and Formula C in mitochondrial biogenesis further suggested that they may have great potential in aging intervention, especially the conditions associated with cognitive function, muscle strength, cardio conditions.

Furthermore, Formula C increased median, mean, and maximum lifespan by 6.7%, 9.5%, and 12.9%, respectively. The significant increase of median survival, compared to the control animals, indicated an improvement in general health in Formula C treated mice without changing daily caloric intact. Extension of maximum survival further supported the health benefit to the rodents exposed to Formula C.

As aging is associated with a functional and metabolic decline, and CR has shown its power of intervention, it is believed that Experiments I-III demonstrate that Formulas A-C, when administered to a subject, can have a beneficial effect on the aging process.

Figure 14:
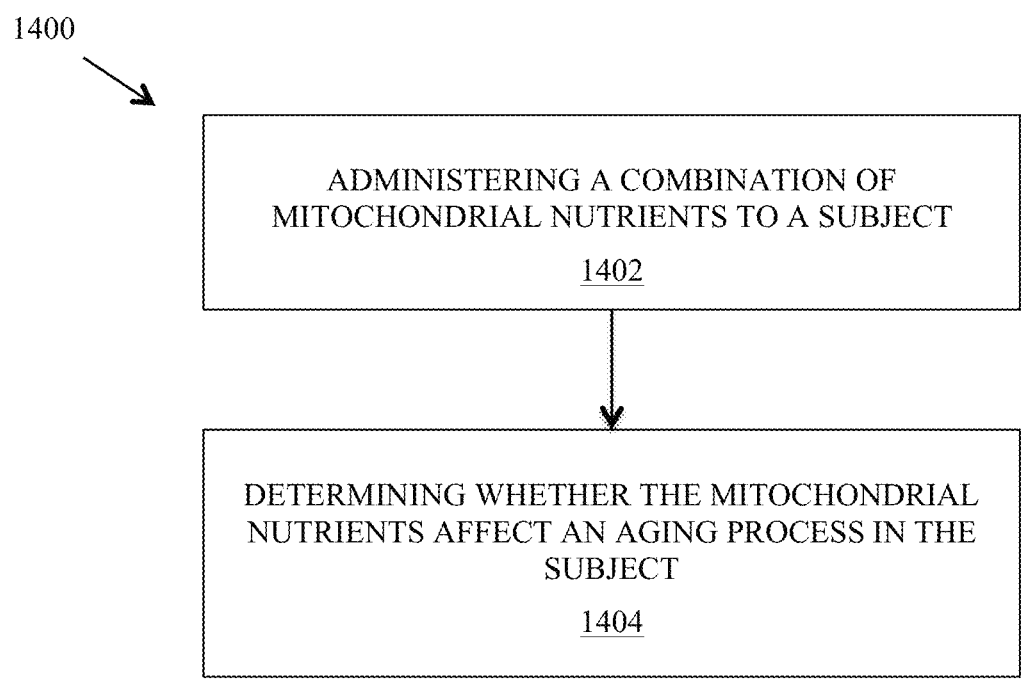
FIG. 14 illustrates a process flow for identifying a combination of mitochondrial nutrients having an affect on an aging process in a subject.

FIG. 14 illustrates an embodiment of a process flow for identifying a combination of mitochondrial nutrients sufficient to affect an aging process in a subject. Process 1400 may include administering a combination of mitochondrial nutrients to a subject (block 1402). Process 1400 may further include determining whether the mitochondrial nutrients affect an aging process in the subject (block 1404). Representatively, determining whether the mitochondrial nutrients affect an aging process in the subject may include performing a strength test to determine whether the combination of mitochondrial nutrients attenuates skeletal muscle impairment caused by an aging process as previously discussed. In still further embodiments, determining whether the mitochondrial nutrients affect an aging process may include performing a gene expression analysis to determine whether the combination of mitochondrial nutrients results in a gene expression profile consistent with a gene expression profile for CR as previously discussed. In still further embodiments, determining may include evaluating a lifespan of the subject to determine whether a median, a mean or a maximum lifespan of the subject is increased with respect to a control subject as previously discussed.

In the preceding detailed description, specific embodiments are described. It will, however, be evident that various modifications and changes may be made thereto without departing from the broader spirit and scope of the claims. The specification and drawings are, accordingly, to be regarded in an illustrative rather than restrictive sense.

What is claimed is:

1. A composition consisting essentially of:
   vitamin D3;
   green tea extract;
   dehydroepiandrosterone; and
   pyrroloquinoline quinone.

2. The composition of claim 1 wherein the amount of pyrroloquinoline quinone is from 10 mg to 20 mg.

3. The composition of claim 1 wherein the amount of vitamin D3 is from 100 IU/kg to 7000 IU/kg, the amount of green tea extract is from 25 mg to 730 mg and the amount of dehydroepiandrosterone is from 15 mg to 200 mg.

4. The composition of claim 1 wherein the concentration of vitamin D3 is from 1.67 mg/kg to 116.67 mg/kg.

5. The composition of claim 1 wherein the concentration of green tea extract is from 0.42 mg/kg to 12.17 mg/kg.

6. The composition of claim 1 wherein the concentration of dehydroepiandrosterone is from 0.25 mg/kg to 3.33 mg/kg.

* * * * *

UNITED STATES PATENT AND TRADEMARK OFFICE
CERTIFICATE OF CORRECTION

PATENT NO. : 9,138,453 B2  
APPLICATION NO. : 14/513136  
DATED : September 22, 2015  
INVENTOR(S) : Xi Zhao-Wilson It is certified that error appears in the above-identified patent and that said Letters Patent is hereby corrected as shown below:

On the Title Page, in Item [56], under Other Publications, please add
--DAHLAN, HASNIZAWATI M., et al., "Proteomic analysis reveals that treatment with tocotrienols reverses the effect of H2O2 exposure on peroxiredoxin expression in human lymphocytes from young and old individuals", Journal of Nutritional Biochemistry, Vol. 23, No. 7, (July 1, 2012), pp. 741-751.
GENAZZANI, ALESSANDRO D., et al., "Might DHEA be Considered a Beneficial Replacement Therapy in the Elderly?", Drugs & Aging, Vol. 24, No. 3, (2007), pp. 173-185.
LEE, SHU-PING, et al., "Effects of tocotrienol-rich fraction on exercise endurance capacity and oxidative stress in forced swimming rats", European Journal of Applied Physiology, Vol. 107, No. 5, (August 25, 2009), pp. 587-595.--

Signed and Sealed this
Fifth Day of April, 2016

Michelle K. Lee
*Director of the United States Patent and Trademark Office*